United States Patent
Goble

(10) Patent No.: US 6,510,854 B2
(45) Date of Patent: Jan. 28, 2003

(54) METHOD OF TREATMENT OF PROSTATIC ADENOMA

(75) Inventor: Nigel M. Goble, Berks (GB)

(73) Assignee: Gyrus Medical Limited, Cardiff (GB)

( * ) Notice: Subject to any disclaimer, the term of this patent is extended or adjusted under 35 U.S.C. 154(b) by 0 days.

(21) Appl. No.: 09/799,358

(22) Filed: Mar. 6, 2001

(65) Prior Publication Data

US 2001/0027317 A1 Oct. 4, 2001

Related U.S. Application Data

(60) Provisional application No. 60/189,880, filed on Mar. 16, 2000.

(51) Int. Cl.$^7$ .............................................. A61B 19/00
(52) U.S. Cl. ........................... 128/898; 606/41; 604/22; 607/101; 607/102
(58) Field of Search ..................... 128/898; 606/40–50; 607/99–104; 604/21, 22

(56) References Cited

U.S. PATENT DOCUMENTS 5,681,282 A * 10/1997 Eggers et al. ............... 604/114
5,807,395 A * 9/1998 Mulier et al. ................ 604/22
6,015,406 A * 1/2000 Goble et al. ................. 606/41
6,091,995 A * 7/2000 Ingle et al. .................. 606/41

* cited by examiner

Primary Examiner—Rosiland S. Kearney
(74) Attorney, Agent, or Firm—Nixon & Vanderhye P.C.

(57) ABSTRACT

A surgical technique for treating bladder outflow obstruction is disclosed in which access is gained to the treatment site via the bladder itself through one or more suprapubic conduits. The disclosed technique includes inserting at least a first conduit suprapubically into the bladder, inserting at least a surgical instrument along the first conduit, distending the bladder with an isotonic fluid, viewing the position of the instrument using remote visualisation means, direct visualisation means, or a combination of the two, and using the surgical instrument to create at least one hole in the prostate gland, thereby to debulk the adenoma. Preferably the procedure is performed using electrosurgery, which offers significant advantages in terms of minimally invasive surgery and patient recovery times in comparison to more conventional forms of surgery.

9 Claims, 6 Drawing Sheets

METHOD OF TREATMENT OF PROSTATIC ADENOMA

This application claims the benefit of U.S. Provisional Appication No. 60/1899,880, filed Mar. 16, 2000, the entire content of which is hereby incorporated by reference in this application.

The present invention relates to the treatment of benign growths in the prostate gland, known clinically as prostatic adenoma.

A common complaint associated with the prostate gland is benign prostatic hyperplasia, or an enlarging of the prostate, resulting in constriction of the urethra and consequent difficulty in urinating. Existing techniques for treating this condition include trans-urethral resectioning of the prostate (TURP for short), a procedure in which an instrument inserted along the urethra of the patient is used to remove the prostate tissue which obstructs the urethra. Typically this procedure is performed using an electrosurgical instrument which resects the prostate tissue, and involves removing the obstructing tissue in a series of thin strips. A disadvantage of this procedure is the consequent removal of virtually all of the urethra in the region of the prostate.

In our U.S. Pat. 6,015,406 which relates inter alia to electrosurgical instruments and their operation for the purpose of debulking, cutting or coagulating tissue, we disclose the use of an electrosurgical instrument having a short, rigid brush electrode to debulk a tumour such as a prostate adenoma. Specifically, we disclose that prostatic adenoma can be treated by drilling a series of holes into the adenoma. The residual tissue bridges will shrink as part of the healing process. Whilst not removing the whole tumour, this technique is safer and quicker than removing the entire adenoma, when treatment is being performed for bladder outflow obstruction, and in addition results in significantly less destruction of the urethra.

The present invention provides a surgical technique for treating bladder outflow obstruction for example, and in one aspect of the present invention access is gained to the treatment site via the bladder itself, as a result of one or more suprapubic conduits.

According to a first aspect of the present invention, there is provided a method of treating prostatic adenoma comprising the steps of:

inserting at least a first conduit suprapubically into the bladder;

inserting at least a surgical instrument along the first conduit;

distending the bladder with an isotonic fluid;

viewing the position of the instrument using at least one of: (a) remote visualisation means, (b) direct visualisation means and (c) a combination of remote and direct visualisation means; and using the surgical instrument to create at least one hole in the prostate gland, thereby to debulk the adenoma.

This technique has the advantage of leaving the urethra and the bladder neck, while the bladder outflow obstruction is alleviated as the tissue within the prostate gland lying adjacent the urethra collapses into the cavities created by the procedure.

Preferably the procedure is performed using electrosurgery, which offers significant advantages in terms of minimally invasive surgery and patient recovery times in comparison to more conventional forms of surgery. One preferred form of electrosurgery is bipolar electrosurgery in which a conductive path between a pair of electrodes located on an electrosurgical instrument is completed by means of a conductive fluid, such as isotonic saline.

Preferably, a second conduit will be inserted suprapubically into the bladder from a site remote to the insertion of the first conduit, and direct visualisation means in the form of an endoscope will be inserted along the second conduit to enable triangulation of the instrument and the visualisation means, this enabling an improved visualisation of the procedure by the surgeon. The electrically conductive fluid will preferably be supplied to the treatment site via one of the conduits. Exhaust of waste products may also be provided via one of the conduits if desired.

In a preferred embodiment of the method, a preoperative image will be obtained using remote visualisation means, such as transrectal ultrasound, in order to obtain an image which may be used to assess the overall shape of the prostate, and to plan the approximate volume of tissue to be removed by drilling. Such remote visualisation means may also be used during the procedure to assess the depth of tissue drilling relative to structures such as the external sphincter which are preferably preserved.

Embodiments of the invention will now be described, by way of example, and with reference to the accompanying drawings, in which.

Figure 1:
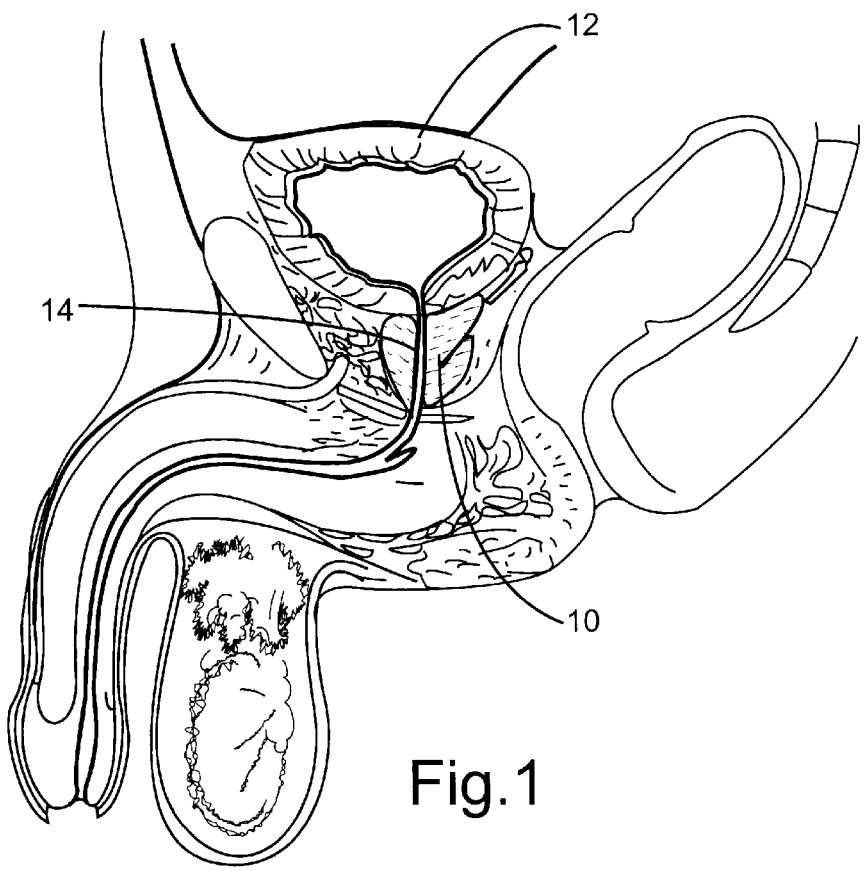
FIG. 1 is a side view of the lower abdominal region of a male.
Figure 2:
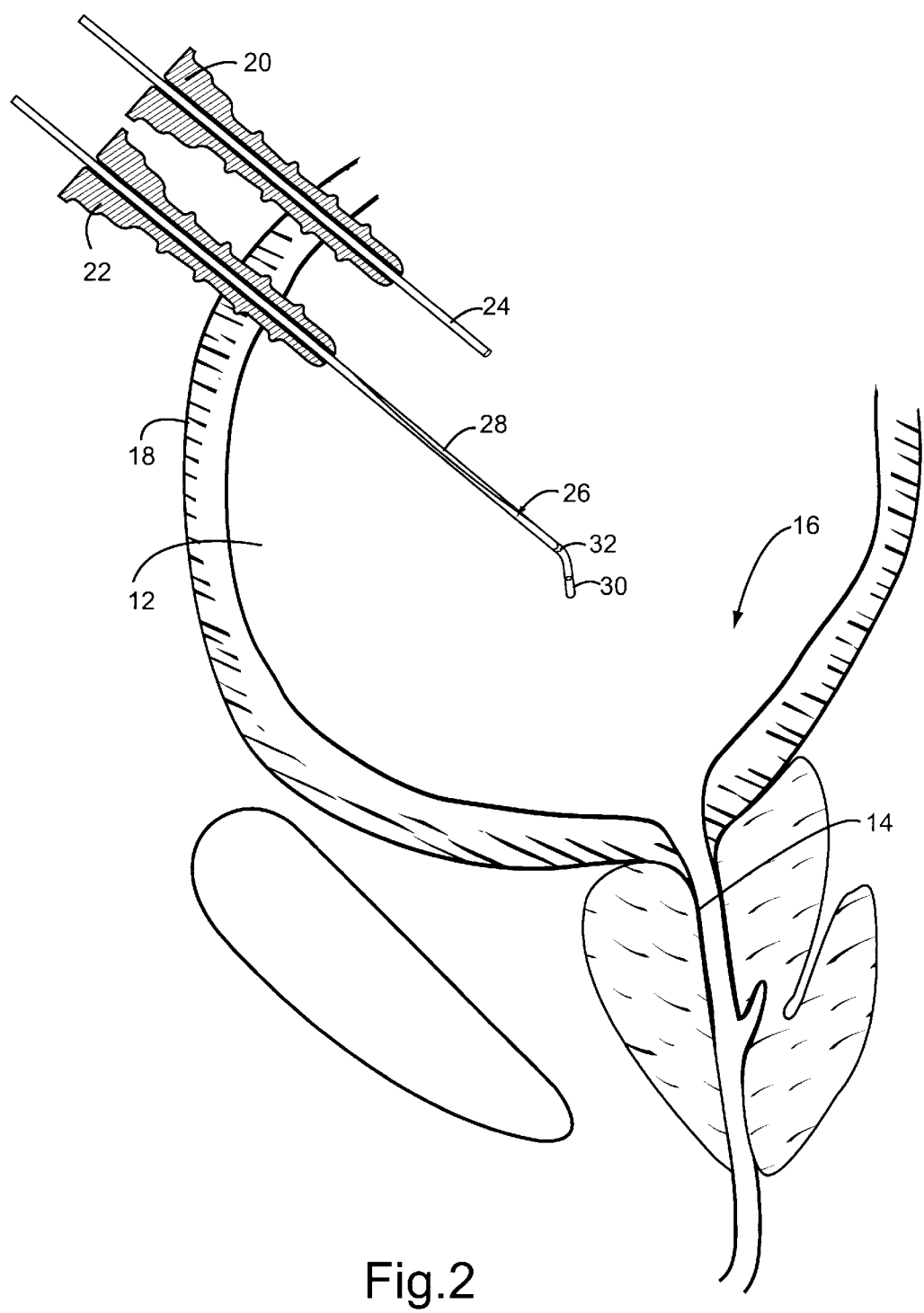
FIG. 2 is a detail of FIG. 1, showing the position of entry of the conduits into the bladder.

Referring now to FIGS. 1 and 2, the prostate gland 10 is a male accessory sex gland which is located just below the bladder 12. The prostate gland 10 opens into the urethra 14, and during ejaculation it serves to secrete an alkaline fluid which forms part of semen. The normal adult prostate is a firm elastic organ roughly pyramidal or conical in shape, and which measures 3–4 cm from apex to base, and is around 4–5 cm in diameter at its widest point. It is customary to divide the gland into two lateral lobs, a median lobe connecting these two, a posterior lobe lying behind the plane defined by the ejaculatory ducts, and an anterior lobe. In actuality, the individual lobes are not clearly demarcated as in lower animals, but for the purposes of elucidating the method of the present invention, the prostate shall be considered to have three lobes: two lateral lobes 10R, 10L and a middle lobe 10M (shown in FIGS. 3 and 5).

Enlargement of the prostate gland 10 causes a consequential constriction of the urethra 14 which passes through the prostate, and a resultant difficulty in passing water. To alleviate this condition the present invention provides for a suprapubic surgical procedure in which one or more holes are drilled into the prostate gland via the bladder neck 16 to reduce the volume of the prostate gland; access to the bladder neck 16 is obtained by the insertion of one or more conduits, known in the art as cannula, through the lower abdomen just above the symphysis pubic 18. In a preferred example of the present invention, two cannulae 20, 22 are provided, cannula 20 providing a conduit for an endoscope 24 in order to provide visualisation of the treatment site, and cannula 22 providing a conduit for an electrosurgical instrument 26. Inserting the two cannulae 20, 22 at spaced-apart locations provides a triangulation of the instrument 26 and the endoscope 24, which is advantageous for viewing purposes. It is however possible to insert the electrosurgical instrument 26 inside a cannula which also contains the endoscope 24, thereby reducing the number of cannulae to one, but this is not preferred in the present surgical procedure because it is desirable to be able to view the electrosurgical instrument 26 from a laterally displaced position. In addition, the bladder 12 is distended by filling it with isotonic saline, via one of the cannulae 20, 22. This distension provides for improved access to the treatment site in the region of the bladder neck 16, and in addition is beneficial to the operation of the electrosurgical instrument, which operates in the presence of a conducting fluid (the urine within the bladder 12 also being conductive, and the method of the present invention therefore being possible to perform in the absence of additionally supplied conductive fluid).

The electrosurgical instrument is generally described in our U.S. Pat. No. 6,015,406, and comprises an elongate semi-flexible and malleable shaft 28, which in the present example is bent slightly toward its distal end to provide a more appropriate angle of attack at the bladder neck 16 for an active electrode 30, situated at the very distal end of the instrument shaft 28 (insertion of the instrument through the cannula is possible because of the semi-flexible nature of the cannula). Radio frequency power from an electrosurgical generator (not shown) is applied between the active electrode 30 and a return electrode 32, proximally spaced from the active electrode, typically by means of a ceramic or other suitable insulating material. Current flows through the isotonic saline between the electrodes 30, 32, and causes heating of the saline. The active electrode 30 has a smaller surface area than the return electrode 32, and as a result, the current density in the region of the active electrode 30 is higher than the current density in the region of the return electrode. The higher current density in the region of the active electrode 30 is higher than the current density in the region of the return electrode. The higher current density in the region of the active electrode 30 results in a higher power density in this region, which in turn causes the formation of a vapor pocket in the region of the active electrode 30. Arcing occurring across the surface of tissue brought within the boundary of the vapour pocket causes the dissociation of tissue into water vapour, known as vaporisation, and this phenomenon may be used to cut (strictly speaking this involves vapourising a small channel, rather than the traditional definition of cutting) of ablate tissue. This type of bipolar electrosurgical system and its operation is known per se, from our U.S. Pat. No. 6,004,319 (the contents of which are hereby incorporated by reference), and will not be described further herein.

Figure 3:
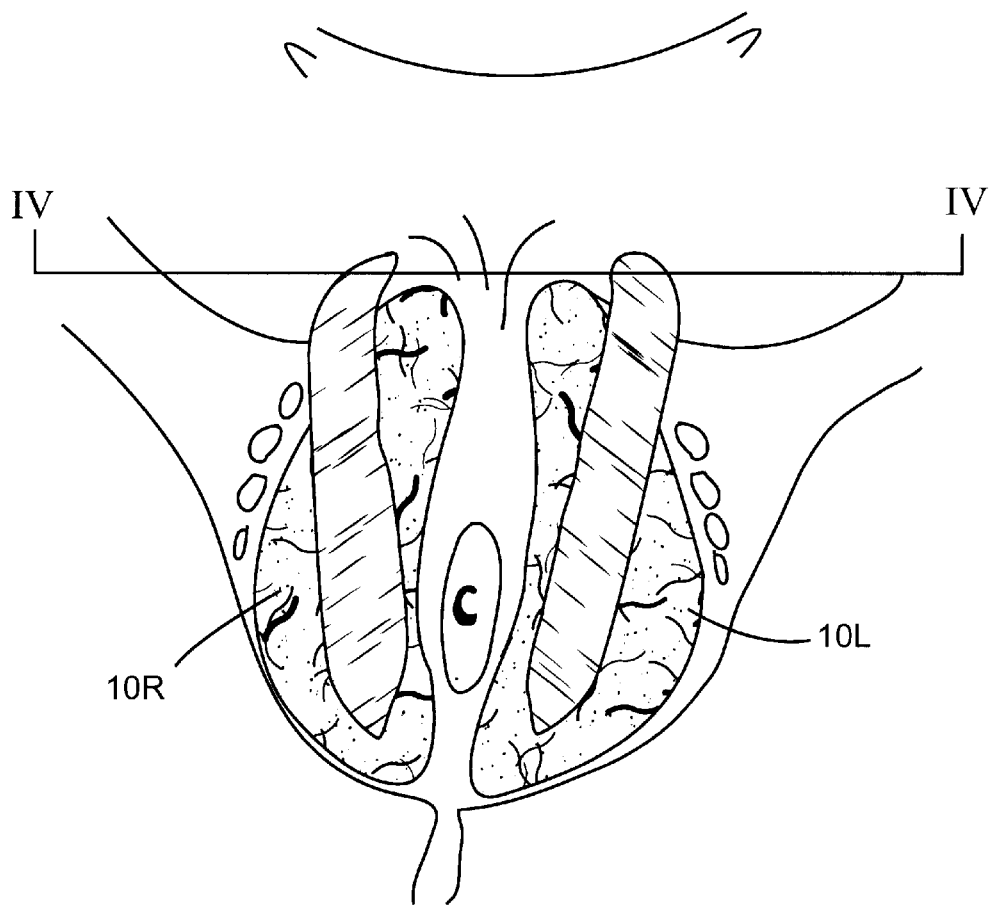
FIG. 3 is a plan view from the direction of the pubis of the prostate gland showing the holes drilled in prostate tissue.
Figure 4:
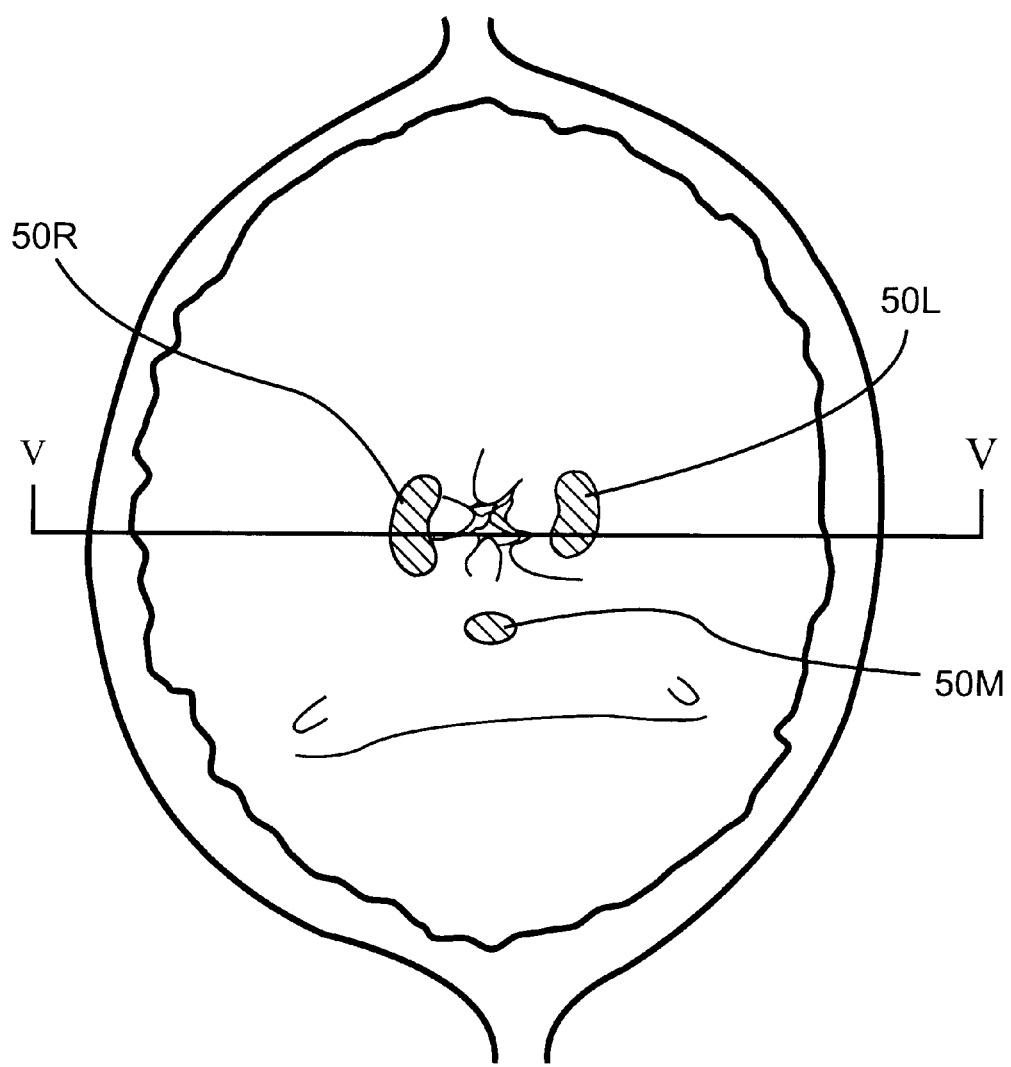
FIG. 4 is a view from IV—IV in FIG. 3.
Figure 5:
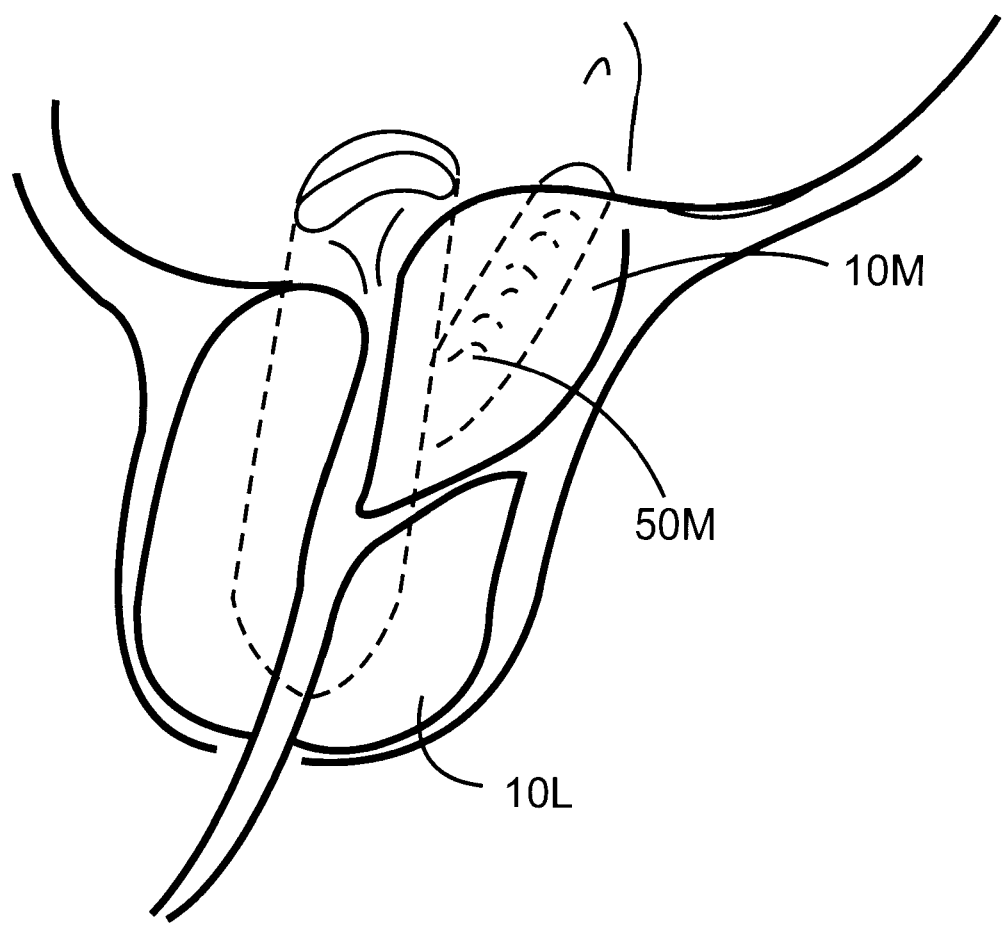
FIG. 5 is a view on V—V in FIG. 4.

Referring now additionally to FIGS. 3 to 5, in accordance with the present invention, a cavity 50 is drilled into each of the lobes 10L, 10R and 10M using the electrosurgical instrument 26. In the present example, the cavities 50 are formed by applying the active electrode 30 of the instrument 26 to the bladder neck, and vapourising tissue in each of the lobes 10L, 10R and 10M of the prostate gland to form a substantially bullet shaped cavity 50L, 50R and 50M respectively in each. The cross sectional area and depth of the cavities 50 will vary from patient to patient in dependence upon, inter alia, the size of the respective lobes 10L, 10R and 10M, and the extent of the outflow obstruction. Typically the cavities 50 will have a cross-sectional area in the shape of a kidney bean (see FIG. 4), with a maximum length of 2 cm and a width approximately half of the length. The angle of the tissue cavity created will depend upon the shape of the prostate gland as it narrows towards its apex (which is located at its base, distally of the bladder).

Because, in the present example, the method by which the cavities 50 are formed is a bipolar electrosurgical system which operates in the presence of an electrically conducting fluid, it is important to ensure that the vaporisation of tissue during the formation of a cavity does not result in the active electrode being trapped within a gas pocket inside a lobe. For this reason it is desirable to progress the formation of the cavities from as broad a base as possible. In the present example, the active electrode 30 of the instrument 26 has a diameter of 3.5 mm, and is therefore considerably smaller than the cross-section of the cavity 50 which it is desired to create within the prostate gland, and this is advantageous in avoiding trapping the active electrode within an air pocket. As an additional safeguard, it is preferable to place the patient in a reverse Trendelenburg position (where the patient has his legs in stirrups, with his feet lower than his abdomen), which will encourage the venting of bubbles from the cavities created by vapourisation of prostatic tissue.

In a preferred embodiment, the shaft 28 of the instrument 26 has markings, typically in the form of a graduated scale to enable a surgeon to assess the depth of penetration of the instrument within the respective lobe.

Preferably an ultrasonic image of the prostate gland is obtained prior to performing the procedure in order to provide an accurate indication of the size of the 10 gland, and therefore the required depth and cross-section of the tissue core to be removed. It is also possible to view the urethra during the procedure using a cystourethroscope, and/or to employ transrectal ultrasound to provide an image of the gland during the procedure.

Figure 6:
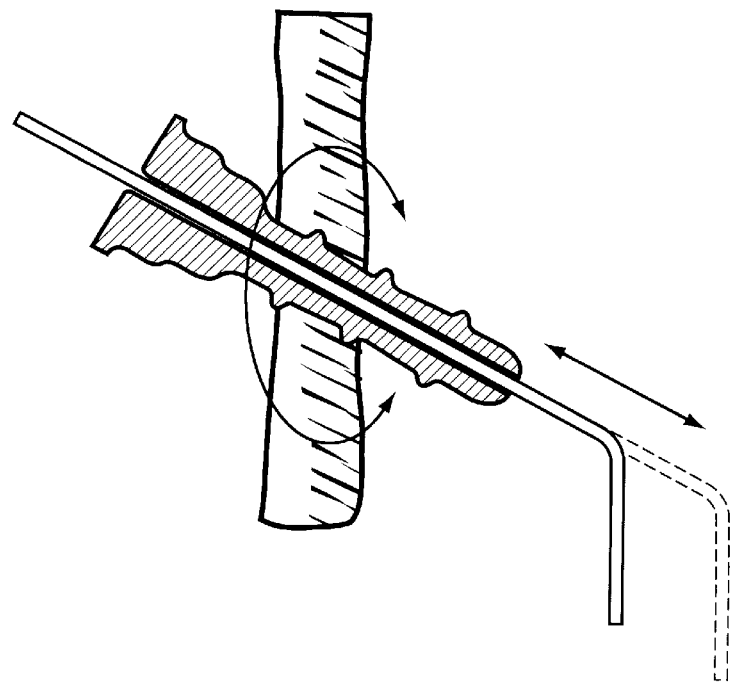
FIG. 6 is.a detail of FIG. 2 illustrating the degrees of freedom available to the surgeon for manipulation of the instrument.
Figure 7:
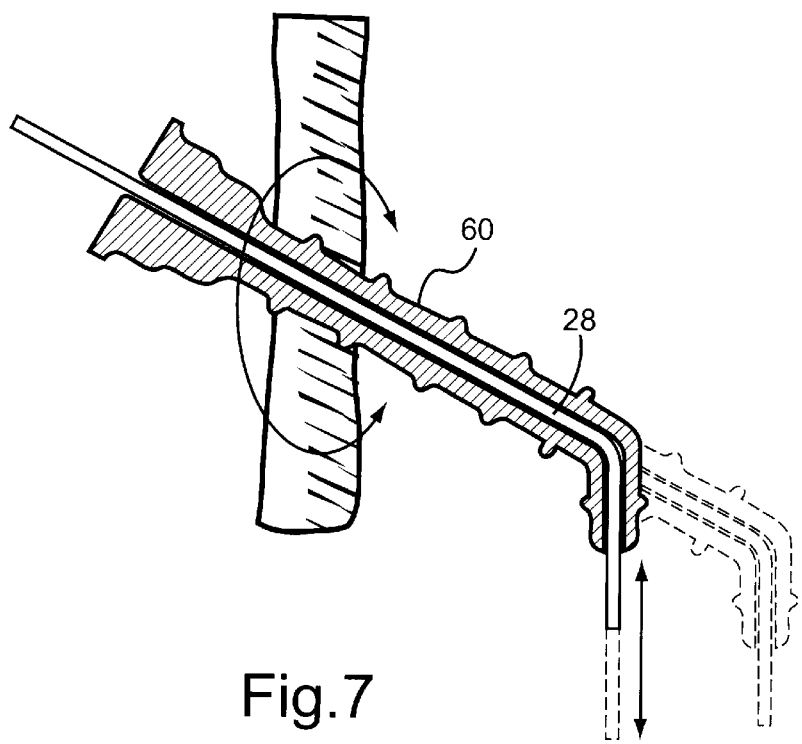
FIG. 7 is a similar view to that of FIG. 6 showing a modification of the instrument shown in FIG. 6.

Referring now to FIG. 6, the surgeon is able to manipulate the active electrode 30 of the instrument 26 with two degrees of freedom; two rotational degrees of freedom, about an axis generally at the point of intersection of the cannula within the tissue wall 40, and one translational, this being provided simply by the ability to move the instrument in and out of the cannula. Generally this will be sufficient manouvreability to create the requisite cavities in the respective lobes. However, it should be noted that in the arrangement of FIG. 6 it is not possible to advance the instrument toward the tissue along an axis defined by the short bent length of the instrument at its distal end. Should this become necessary an arrangement as shown in FIG. 7 is preferred, in which the cannula 60 is longer and is bent at its distal end. In addition the cannula 60 is relatively rigid. This enables the relatively flexible shaft 28 of the instrument to conform to the shape of the cannula 60, which therefore provides for the ability to advance the instrument along the direction of the axis of the shaft at its distal end.

Figure 8:
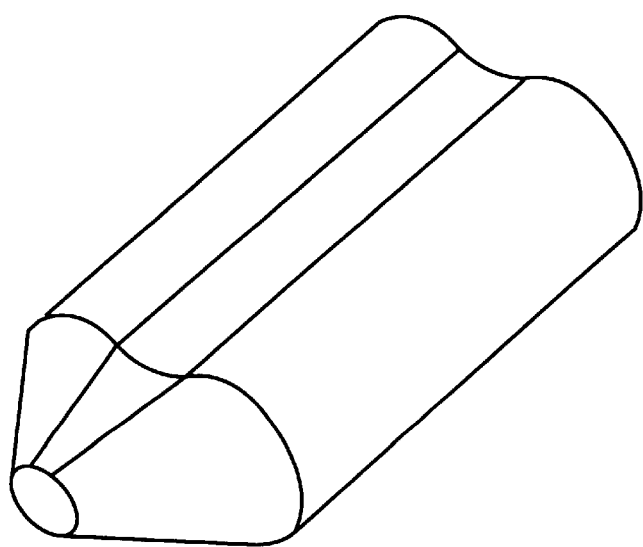
FIG. 8 is a perspective view of the tissue volume typically removed by an embodiment of the method of the present invention.

Referring now to FIG. 8, a perspective view of the tissue core which may typically be removed to create the cavities 50 is illustrated. A typical volume of tissue which might be removed to create a cavity in one of lateral lobes 10L, 10R would be in the region of 6 cm$^3$.

Although the present invention has been described in terms of a particular embodiment and process, it is not intended that the invention be limited to that embodiment. Modifications of the embodiment and process within the spirit of the invention will be apparent to those skilled in the art. The scope of the invention is defined by the claims that follow.

What is claimed is:

1. A method of treating prostatic adenoma comprising the steps of:
    inserting at least a first conduit suprapubically into the bladder;
    inserting at least a surgical instrument along the first conduit into the bladder;
    distending the bladder with an isotonic fluid;
    viewing the position of the instrument using visualisation means; and
    applying the surgical instrument to the prostrate gland via the bladder to create at least one hole in the prostate gland, thereby to debulk the adenoma.

2. A method according to claim 1, wherein the instrument is an electrosurgical instrument, and the method additionally comprises the step of supplying radio frequency power to the instrument.

3. A method according to claim 2 wherein the isotonic fluid is electrically conducting, and the instrument comprises at least a pair of electrodes, and the method additionally comprises the step of completing a conduction path between the electrodes using the conductive fluid.

4. A method according to claim 3 wherein the visualisation means is a direct visualisation means.

5. A method according to claim 4 wherein the method additionally comprises the steps of:
    inserting a second conduit suprapubically into the bladder, the first and second conduits being offset from each other;
    inserting an endoscope along the second conduit; and
    viewing the surgical instrument with the endoscope.

6. A method according to claim 3 wherein each hole is made in the prostate gland in the vicinity of the bladder neck.

7. A method according to claim 3 wherein the visualisation means is indirect.

8. A method according to claim 7 wherein the visualisation means is ultra sound.

9. A method according to claim 3 wherein the method additionally comprises the step of assessing the size of the prostate by obtaining a trans-rectal ultrasound image prior to the creation of a cavity.

* * * * *